(12) United States Patent
Haas

(10) Patent No.: US 6,392,062 B1
(45) Date of Patent: May 21, 2002

(54) METHOD FOR CARRYING OUT HOMOGENEOUSLY CATALYZED REACTIONS

(75) Inventor: Thomas Haas, Frankfurt (DE)

(73) Assignee: Degussa AG, Düsseldorf (DE)

( * ) Notice: Subject to any disclaimer, the term of this patent is extended or adjusted under 35 U.S.C. 154(b) by 1 day.

(21) Appl. No.: 09/711,133

(22) Filed: Nov. 14, 2000

(30) Foreign Application Priority Data

Jan. 27, 2000 (DE) .......................................... 100 03 317

(51) Int. Cl.[7] .............................................. C07D 493/00
(52) U.S. Cl. ........................................................ 549/464
(58) Field of Search ........................................ 549/464

(56) References Cited

PUBLICATIONS

Charles N. Satterfield, *Heterogeneous Catalysis in Industrial Practice*, 2nd Edition, 1991, Table of Contents and Chapter 1, pp. 1–16.

Agostino Gianetto, et al., *Multiphase Chemical Reactors Theory, Design, Scale–up*, 1986, p. 9.

*Primary Examiner*—Amelia Owens
(74) *Attorney, Agent, or Firm*—Smith, Gambrell & Russell, LLP

(57) ABSTRACT

The conversion rate of a homogeneously catalyzed reaction in which an educt is converted into a reaction product with addition or cleavage of a reaction partner or under isomerization in a liquid phase that contains an effective amount in dissolved form of a catalyst suitable for the reaction can be significantly increased in that the liquid phase containing the educt and homogeneous catalyst and, to the extent required, reaction partners [2nd] to be attached are brought into contact with a stationary or moved bed consisting of porous particles, especially particles with a pore volume of 0.1 to 3 ml/g. The liquid phase is preferably conducted in a trickle bed operation over a stationary fixed bed.

23 Claims, No Drawings

METHOD FOR CARRYING OUT HOMOGENEOUSLY CATALYZED REACTIONS

INTRODUCTION AND BACKGROUND

The present invention relates to a method for carrying out homogeneously catalyzed reactions in which an educt is converted into a reaction product with or splitting off of a reaction partner or under isomerization in a liquid phase that contains an effective amount of a dissolved catalyst suitable for the desired reaction. The reaction is further accelerated by the method of the invention.

Numerous chemical reactions are carried out for the purpose of accelerating them in the presence of a homogeneous or heterogeneous catalyst. Homogeneous catalysts are those that are molecularly dispersed in the reaction medium, e.g., dissolved in a liquid reaction medium. Heterogeneous catalysts are insoluble in a liquid reaction medium and comprise solid surfaces and particulate substances that comprise the actual catalytically active centers. In as far as two different reactions are not to be carried out substantially simultaneously or in direct succession in a liquid reaction medium, an expert in the art will decide to use a single, that is, a homogeneous or a heterogeneous catalytic system. In order to carry out, e.g., an acid-catalyzed reaction in liquid phase the reaction medium accordingly contains either a dissolved acid as homogeneous catalyst or, as an alternative thereto, the reaction is carried out using a heterogeneous catalyst containing acidic activity centers.

The concept that is customarily employed today to describe the mode of action of a catalyst is the assumption that a center is present on the catalyst which center forms a complex with the reactant and from which the products desorb after the reaction, with the original center being reestablished (see "Heterogeneous Catalysis in Industrial Practice", Charles N. Satterfield, $2^{nd}$ ed. (1991), p. 8). According to this concept the conversion rate was related as turnover frequency (TON) to a catalytic center (see "Heterogeneous Catalysis in Industrial Practice", Charles N. Satterfield, $2^{nd}$ ed. (1991), p. 15). An expert in the art would accordingly expect, given the presence of two catalysts or catalytic centers, that the conversion rates of these two would add together.

The so-called heterohomogeneous catalysis is also known (see, e.g., "Heterogeneous Catalysis in Industrial Practice", Charles N. Satterfield, $2^{nd}$ ed. (1991), pp. 13/14) according to which a heterogeneous catalyst forms radicals, for example, and these radicals initiate a chain reaction in a liquid reaction medium. In the case of heterohomogeneous catalysts the catalytic reaction on the heterogeneous catalyst can also interact with a homogeneous reaction. However, it is not known and is also not rendered obvious by this document that a reaction that has already been catalyzed homogeneously can be further accelerated by porous solid particles that are present and that for their part are not catalytically active or only moderately catalytically active alone as catalyst for the reaction under the reaction conditions in a manner similar to that of the case of the accelerating of the thermal decomposition of gases by the addition of a further inert gas (see "Heterogeneous Catalysis in Industrial Practice", Charles N. Satterfield, $2^{nd}$ ed. (1991), p. 9).

An object of the invention accordingly is making available a method for carrying out a homogeneously catalyzed reaction of an educt with formation of a reaction product in which the action of the homogeneous catalyst is reinforced and the reaction is further accelerated therewith.

The fact that the effect in accordance with the invention concerns a reinforcing action of the catalyst and not an additional catalyst in accordance with the above definition can be recognized from the fact that the conversion rate is not increased additively by the conversion rate of an additional catalyst, that is, of the porous solid particles, but rather is elevated or reinforced in a multiplicative manner by a certain factor.

SUMMARY OF THE INVENTION

The above and other objects of the invention can be achieved in that the reaction is carried out in the presence of porous solid particles, especially a fixed bed consisting of such porous particles. It is a feature of the invention that the porous solid particles do not act primarily by inserted or adsorbed active centers such as acid or metal centers but rather solely by the three-dimensional structure of the porous particles. An interaction between the three-dimensional structure and/or activity centers of the porous particles with the homogeneous catalyst is not excluded.

Accordingly, the invention features a method for carrying out a homogeneously catalyzed reaction in which an educt is converted into a reaction product with addition or splitting off of a reaction partner or under isomerization in a liquid phase that contains an effective amount of a catalyst suitable for the reaction in dissolved form, which method is characterized in that the educt and the liquid phase containing the homogeneous catalyst as well as, if required, reaction partners to be added are brought into contact with a stationary or moving bed of porous particles, especially conducted through a stationarily arranged fixed bed.

The homogeneously catalyzed, liquid reaction medium as well as, if necessary, reaction partners to be added to an educt can be brought into contact with the porous solid particles in any manner desired in discontinuous or continuous processes. It is therewith possible to allow the liquid reaction medium to stand above a stationary or flowing bed of porous solid particles and to conduct the liquid reaction medium over this fixed bed or to keep the porous solid particles in suspension analogous to a suspension catalyst in the liquid reaction medium.

According to a preferred embodiment the porous solid particles are arranged in a reactor as a fixed bed and liquid reaction medium conducted in a flooded state (=bubble mode of operation) or by trickling (=trickle bed mode of operation) over the fixed bed. The reaction rate is significantly increased by the method of the invention.

The trickle bed mode of operation is especially preferred. Since the liquid holdup in a trickle bed reactor is generally 5 to 20% of the fixed bed volume (see "Multiphase Chemical Reactors", ed. A. Gianetto and P. L. Silveston, Hemisphere Publ. Corp. (1986), p. 9), the homogeneously catalyzed reaction can be accelerated by more than a factor of 10, as results from the examples in accordance with the invention. The trickle bed mode of operation is particularly suitable in systems in which a gaseous reaction partner such as hydrogen in the case of a hydrogenation participates in addition to the liquid reaction medium.

In addition to the presence of porous solid particles, it is an essential feature of the invention that the reaction is catalyzed by a homogeneous catalyst dissolved in the liquid reaction medium. The method of the invention is substantially independent of the type of catalyst dissolved in the liquid reaction medium and of the catalyzed reaction.

It was determined that acid-catalyzed reactions in aqueous systems can be significantly accelerated even in the absence of an acid catalyst on porous solids added to the reaction medium. In this instance the water functions as homogeneous, acidic catalyst.

The reaction can be, e.g., an acid-catalyzed reaction such as, e.g., an etherification, ether cleavage, esterification, ester cleavage, reesterification, acetalization,, ketalization, iminization, hydrolysis of imines, nitriles and anhydrides, dehydration of alcohols and isomerization of olefinic compounds. In the case of an acid-catalyzed reaction the reaction medium contains an active amount of an organic or inorganic acid, especially a lower carboxylic acid or mineral acid in dissolved form. Even the protons of the water alone can function as acid. The selection and amount of the acidic catalyst are a function of the system considered and of the desired reaction conditions and constitute subject matter for expert optimization.

Reactions catalyzed homogeneously by bases such as, e.g., the hydrolysis of amides or the attachment of hydrogen cyanide, aldehydes, ketones and activated olefins can be further accelerated by the method of the invention using, e.g., alkali hydroxides as catalyst.

Even homogeneously catalyzed hydrogenations are accessible to the method of the invention. Suitable homogeneous catalysts are, e.g., noble metal compounds soluble in the reaction medium and compounds of iron, cobalt and nickel.

Other homogeneously catalyzed reactions assessable to the method of this invention are dehydrogenation reactions and oxidation reactions, e.g., such reactions using soluble compounds of elements from the series of chromium, vanadium, molybdenum and tungsten and hydroformulations, e.g., such reactions in the presence of ligand-stabilized cocarbonyl compounds.

The porous solid particles result, independently of whether they themselves catalyze the desired reaction not at all or to a greater or lesser degree, in a significant increase in the acceleration of the reaction; in the case of a self-catalysis by the solid particles a synergistic effect of the acceleration of the homogeneously catalyzed reaction is achieved.

According to a further embodiment of the invention such substances are used as porous solid particles that on the one hand further accelerate a homogeneously catalyzed first reaction by their three-dimensional structure but on the other hand also comprise activity centers that heterogeneously catalyze the second reaction that occurs in parallel or subsequently. This embodiment is particularly advantageous in an acid-catalyzed reaction if unsaturated compounds formed as byproduct are to be immediately hydrogenated during the homogeneously catalyzed first reaction—in this instance the solid particles contain activity centers that are active as regards hydrogenation and consist of noble metals and/or nickel or cobalt and the hydrogenation taking place as the second reaction is catalyzed heterogeneously.

DETAILED DESCRIPTION OF INVENTION

The porous solid particles to be used in accordance with the invention contain pores from the series of macropores with a pore diameter of greater than 50 nm (50 to 10,000 nm), mesopores with a pore diameter in a range of 2 to 50 nm and micropores with a pore diameter of less than 2 nm. Solids with a high number of meso- and micropores are especially advantageous. The pore volume of the solids is advantageously in a range of 0.1 to 3 ml/g, preferably in the range of 0.3 to 1.5 ml/g. According to a preferred embodiment 10 to 100% of the porous consist of micropores and mesopores and 40 to 80% of the pore volume is preferably formed by mesopores. The micropore volume can be determined from the nitrogen adsorption isotherm at the temperature of liquid nitrogen by comparison with a standard isotherm according to the t-plot method of De Boer (see De Boer et al. in J. of Colloid and Interface Science 21, 405–44 (1966)) according to DIN 66135, part 2 (draft—April 1988). The determination of the mesopore volume and of the pore distribution can take place from the nitrogen desorption isotherm according to Barett, Joyner and Halenda in accordance with DIN 66134 (February 1998). The specimen used to determine the micropore volume and mesopore volume is treated prior to the measurement 1 h at 200° C. in a vacuum (less than 1.3 Pa). The measurement takes place, e.g., in an "ASAP 2400"device of the Micromeritics company, Norcross, Ga. (USA). The macropores are determined by mercury intrusion according to DIN 66133 or ASTM D 4284.

The material of the porous solid particles is customarily substantially inert to the considered reaction and to the substances used. It is, e.g., activated carbon, oxide, silicate or metallic materials or porous multi-component systems. Activated carbons, oxide substances such as $TiO_2$, $Al_2O_3$ and $SiO_2$ and silicate substances such as Al silicates, zeolites and titanium silicates are especially preferred and commercially obtainable in different porosities. An expert in the art will also make the selection of substances dependent on, in addition to the porosity, whether the solid is to have an additional function in the considered reaction. If required, the substance is post-treated in this regard, e.g., by doping with heterogeneously, catalytically active elements or compounds such as a platinum metal for producing a hydrogenating activity.

Aside from the contact time of the liquid reaction medium on the porous solid the reaction conditions including the molar ratio of the educts, reaction partners, solvents, temperature and pressure are a function of the desired reaction and are readily assessable to an expert in the art from the pertinent professional literature. The contact time can be readily determined by optimization.

As follows from the examples and reference examples presented in the following, the reaction is significantly accelerated by the use, in accordance with the invention, of a fixed bed consisting of porous solids. At the same time the selectivity is multiply increased by the acceleration of the target reaction.

The advantages of the invention reside in its broad applicability, the increase in the acceleration of the homogeneously catalyzed reaction, the possibility of achieving a greater selectivity as well as in the capability of combination with a heterogeneous, catalyzed reaction.

EXAMPLES

Comparative Example 1 (CE1)
Acid-catalyzed Dehydration of Sorbitol 1.5 kg of a 20% by weight aqueous D-sorbitol solution as well as 15 g propionic acid (=5% by weight relative to D-sorbitol) were placed in a 2 liter autoclave as homogeneous catalyst; 3 g of a Pd-activated carbon catalyst (Pd content 3% by weight) were added. The reaction mixture was heated to 250° C. and agitated 1.5 h at 8 Mpa hydrogen pressure. After the mixture had cooled off the hydrogenating catalyst was filtered off. The D-sorbitol conversion was 71%. Relative to the reactor volume and a reaction time the conversion was 94.7 g/l·h. The selectivity of dianhydrosorbitol was 8% relative to the sorbitol conversion.

Comparative Example 2 (CE2)

CE1 was repeated without the presence of propionic acid. The weakly acidic sorbitol itself functioned as homogeneous catalyst. The conversion of D-sorbitol was 46% and 61.2 g/l·h. The selectivity of dianhydrosorbitol was 4% relative to the conversion of sorbitol.

Comparative Example 3 (CE3)

CE1 was repeated with the difference that the hydrogenating catalyst was omitted. The conversion of D-sorbitol was 73%, corresponding to 97.3 g/l·h. However, 10% of a yellow polymer was produced in addition to anhydrosorbitol.

Comparative Example 4 (CE4)

CE1 was repeated with the difference that the reaction time was 3.5 h. The conversion of D-sorbitol was 95%, corresponding to 54.3 g/l·h. The selectivity of dianhydrosorbitol was 17% relative to the conversion of sorbitol.

Comparative Example 5 (CE5)

CE2 was repeated with the difference that the reaction time was 3.5 h. The conversion of D-sorbitol was 78%, corresponding to 44.5 g/l·h. The selectivity of dianhydrosorbitol was 11% relative to the conversion of sorbitol.

Example 1

70 ml activated carbon extrusion blanks were placed in a reaction tube having an 18 mm inside diameter and 91 ml effective volume. The activated carbon has a specific surface of 1530 m$^2$/g and the following pore volumes: Micropores 0.68 ml/g, mesopores 0.26 ml/g, macropores 0.36 ml/g. The activated carbon was doped with 0.05% by weight palladium. 70 ml of such a charge of activated carbon was filled into the reactor. An aqueous solution containing 20% by weight D-sorbitol and 5% by weight propionic acid catalyst was added at the top together with the hydrogen gas. The pressure was 80 Mpa and the hydrogen flow 20 Nl/h. The liquid flow was 47 ml/h. The reaction tube was heated with a double jacket and the inside temperature of the reactor was 250° C. The reaction mixture was analyzed by gas chromatography. A D-sorbitol conversion of 96% resulted, corresponding to a conversion of 129 g/l·h relative to the fixed bed volume and the time. The selectivity of dianhydrosorbitol was 31% relative to the conversion of sorbitol.

Given a liquid portion in the trickle bed reactor of 5 to 20% in accordance with the literature, a residence time of the liquid on the fixed bed and therewith a reaction time in the range of 0.075 to 0.3 h is determined at the indicated flow of 47 ml/h. In contrast thereto, in comparative example 1 the reaction time was 1.5 h and, moreover, a lesser conversion and lower selectivity were achieved. As CE4 shows, without the addition of a porous solid an increase of the reaction time by a factor of 2.3 becomes necessary to achieve approximately the same conversion. This comparison shows the surprising effect obtained in accordance with the invention.

Example 2

Example as repeated but the reaction mixture contained no propionic acid. The weakly acidic sorbitol itself functioned as homogeneous catalyst. The D-sorbitol conversion was 76% or 102 g/l·h (g sorbitol per 1 fixed bed and hour). The selectivity of dianhydrosorbitol was 91% relative to the sorbitol conversion. As CE5 shows, without the addition of a porous solid an increase of the reaction time by a factor of 2.3 is also necessary here in order to achieve approximately the same conversion.

Further variations and modifications of the foregoing will be apparent to those skilled in the art and are intended to be encompassed by the claims appended hereto.

German priority application 100 03 317.2 is relied on and incorporated herein by reference.

I claim:

1. A method for carrying out a homogeneously catalyzed reaction in a liquid phase in which an educt is converted into a reaction product with addition or cleavage off of a reaction partner or under isomerization comprising:

forming a liquid phase that contains an effective amount in dissolved form of a catalyst suitable for the homogeneously catalytized reaction, bringing the liquid phase containing the educt and homogeneous catalyst, into contact with a stationary or moving bed consisting of porous particles.

2. The method according to claim 1, further comprising conducting said liquid phase over said stationary fixed bed in trickle bed operation.

3. The method according to claim 1, wherein an acid-catalyzed reaction selected from the consisting of etherification, ether cleavage, esterification, ester cleavage, reesterification, acetalization, iminization, dehydration of alcohols and hydrolysis of acetals, imines and nitriles is carried out using an inorganic or organic acid dissolved in said liquid phase as catalyst.

4. The method according to claim 2, wherein an acid-catalyzed reaction selected from the consisting of etherification, ether cleavage, esterification, ester cleavage, reesterification, acetalization, iminization, dehydration of alcohols and hydrolysis of acetals, imines and nitriles is carried out using an inorganic or organic acid dissolved in said liquid phase as catalyst.

5. The method according to claim 1, wherein a homogeneously catalyzed hydrogenation is carried out in which said liquid phase containing a homogeneous hydrogenating catalyst and an educt is conducted in the presence of hydrogen over a fixed bed consisting of porous particles.

6. The method according to claim 2, wherein a homogeneously catalyzed hydrogenation is carried out in which said liquid phase containing a homogeneous hydrogenating catalyst and an educt is conducted in the presence of hydrogen over a fixed bed consisting of porous particles.

7. The method according claim 1, wherein said fixed bed comprising activated carbon particles or oxide or silicate particles.

8. The method according to claim 2, wherein said fixed bed comprising activated carbon particles or oxide or silicate particles.

9. The method according claim 3, wherein said fixed bed comprising activated carbon particles or oxide or silicate particles.

10. The method according to claim 4, wherein said fixed bed comprising activated carbon particles or oxide or silicate particles.

11. The method according to claim 1, wherein said fixed bed particles have a pore volume in a range of 0.1 to 3 ml/g.

12. The method according to claim 2, wherein said fixed bed particles have a pore volume in a range of 0.1 to 3 ml/g.

13. The method according to claim 3, wherein said fixed bed particles have a pore volume in a range of 0.1 to 3 ml/g.

14. The method according to claim 4, wherein said fixed bed particles have a pore volume in a range of 0.1 to 3 ml/g.

15. The method according to claim 5, wherein said fixed bed particles have a pore volume in a range of 0.1 to 3 ml/g.

16. The method according to claim 11, wherein 10 to 100% of the pore volume is formed by micropores and mesopores.

17. The method according to claim 2, wherein 10 to 100% of the pore volume is formed by micropores and mesopores.

18. The method according to claim 3, wherein 10 to 100% of the pore volume is formed by micropores and mesopores.

19. The method according to claim 4, wherein 10 to 100% of the pore volume is formed by micropores and mesopores.

20. The method according to claim 5, wherein 10 to 100% of the pore volume is formed by micropores and mesopores.

21. The method according to claim 1 wherein an additional coreactant is present.

22. A method for accelerating a homogeneously catalyzed reaction comprising carrying out said reaction in the liquid phase with a dissolved catalyst for the reaction and in the presence of porous solid particles have macropores with a pore diameter of greater than 50 nm, mesopores with a pore diameter of 2 to 50 nm and micropores with a pore diameter of less than 2 nm.

23. A method for accelerating a homogeneously catalyzed reaction comprising carrying out said reaction in the liquid phase which functions as a catalyst and in the presence of non-catalytic porous solid particles having macropores with a pore diameter of greater than 50 nm, mesopores with a pore diameter of 2 to 50 nm and micropores with a pore diameter of less than 2 nm.

* * * * *